United States Patent [19]

Albarella et al.

[11] Patent Number: 5,021,586

[45] Date of Patent: Jun. 4, 1991

[54] DITHIOPHENYLPYRROLE DERIVATIVE MONOMERS FOR PREPARING SEMI-CONDUCTING POLYMERS

[75] Inventors: James P. Albarella; Nan-Horng Lin, both of Elkhart, Ind.

[73] Assignee: Miles, Inc., Elkhart, Ind.

[21] Appl. No.: 331,345

[22] Filed: Mar. 31, 1989

[51] Int. Cl.$^5$ .......................................... C07D 409/14
[52] U.S. Cl. .................................. 548/527; 528/380; 252/500
[58] Field of Search ........................................ 548/527

[56] References Cited

PUBLICATIONS

Patil. et al., Chem. Rev. 1988 vol. 88(1) 184–200.
Patil. et al., Synthetic Metals 20(1987) 151–159.
Bargon, et al., IBM J. Ros Devolop. 27th Jul., 1981
Patil. JACS, 1987 109 1858–9.
Audebart, et al., J. Chem. Soc. Commun. 1986, 887–9
Wrighton Science vol. 231, 1986 31 to 37.
B. Jan. et al., Nouveau J. Chemo. 8, 1984 502–3.
Genies, et al., Senthetic Metal 10, 1984 21–30.
Bidan et al., Synth. Mat. 15, 51 (1986).
Wattman, et al., J. Phys. Sci. 1984 4343–46.
Tourillon et al., J. Polymer Sci. 23, 33–39, (1984).
Anderson, et al., Synthesis Appl. 1984 pp. 353–363.
Diaz et al., J. Glataanl Chem. 133 (1982) 233–9.
B. Jan. etal., Tet. Let. 25(6) 735–6, 1985.
Mapchi Advanced Organic Chemistry (McGraw Hill, 1968) pp. 199–200.
Aldrich Ad. J. Med. Chem. 33(6), Jun. 1990 Back Cover.
Katritzky, Handbook of Heterocyclic Chemistry, (Progammon Press, Ltd.) pp. 248–51 (1985).
Xu et al., "Pyrrole Chem.", Tetrahed. Lett. vol. 22 No. 49 pp. 4899–4900 (1981).
Rohach et al., Tetrahed. Lett. vol. 22 Oc. 49 pp. 4901–4904 (1981).
Muchowski et al., Tetrahed. Lett. vol. 24, No. 33 pp. 3455–3456 (1983).
McLeod et al., Polymer, vol 27, (Mar.) pp. 455–148 (1986).

*Primary Examiner*—Nicholas S. Rizzo
*Assistant Examiner*—E. C. Ward
*Attorney, Agent, or Firm*—Roger N. Coe

[57] ABSTRACT

The present invention relates to a number of innovative electrophilic substitution reactions involving 2,5-dithienylpyrrole (2,5-DTP). More specifically, these reactions are used in the synthesis of monomers for preparing functionalized conducting organic polymers.

The elctrophilic substitution reactions in this invention are accomplished under conditions not requiring the use of N-1 pyrrole blocking groups to direction reaction at the pyrrole C-3 position. This is because the steric bulk of the 2,5-dithienyl groups prevent N-acylation and therefore direct reactions with electrophiles at the pyrrole C-3 position.

The reaction conditions chosen have also demonstrated a greater regioselectively towards functionalization at the pyrrole 3-position than the basic reaction conditions suggested in the prior art. This result may be explained by an activation of the pyrrole 3-position towards electrophilic substitution. This is attributed to an electron donating resonance contribution of the 2,5 thienyl groups.

Other advantageous reaction conditions have been discovered which direct electrophilic substitution preferentially at the pyrrole or thiophene groups depending upon the amount of acidic catalyst.

2 Claims, No Drawings

DITHIOPHENYLPYRROLE DERIVATIVE MONOMERS FOR PREPARING SEMI-CONDUCTING POLYMERS

BACKGROUND OF THE INVENTION

1. Field of the Invention

The present invention relates to a number of innovative electrophilic substitution reactions involving 2,5-dithienylpyrrole (2,5-DTP). More specifically, these reaction are used in the synthesis of monomers which in turn can be used to synthesize functionalized conducting organic polymers.

2. Discussion of the Prior Art

I. Organic Conducting Polymers

The present case relates to and is an improvement of U.S. Ser. No. 114,011, now U.S. Pat. No. 4,886,623, "Functionaized Conducting Polymers and Their Use in Diagnostic Devices" by Albarella, et al. The Albarella patent application is hereby incorporated by reference.

Organic conducting polymers are synthesized from specialized monomers which are polymerized chemically, such as in the synthesis of polyacetylene, or electrochemically, such as in the synthesis of polypyrrole and polythiophene. Once polymerized, conducting polymers can be covalently functionalized with an enzyme, antigen or an ion specific binding site. The resulting functionalized conducting organic polymer can be used in diagnostic assays to selectively determine the presence and concentration of a specific analyte.

Functionalized conducting polymers can determine an analyte by measuring the change in conductivity of the polymer. The change in conductivity can arise either from the transduction of vibrational excitation (which is induced in the covalently-bound functionality by the reaction of the functionality with the analyte) or alternatively from secondary reaction effects between the covalently bound functionality and the analyte, such as in the generation of hydrogen peroxide.

Conducting polymers can also be useful in technical fields relating to batteries, display devices, corrosion prevention in metals and semiconductors and in microelectronic devices such as diodes, transistors, sensors, light emitting devices and energy conversion and storage elements. However, present day organic conducting polymers possess several limitations that have hindered the expansion of these substances into these and other potential applications.

II. Design Considerations In Synthesizing Conducting Polymers

Conducting organic polymers are generally amorphous, disordered materials. Therefore if bulk conductivity is to be sustained, charge transport must occur between the polymer strands as well as along single polymer strands. The probability of interchain charge transport is directly related to the distance between the chains, and the distance between polymer chains is acutely sensitive to and dependent upon the nature and size of the dopant counterion and the character and steric requirements of the substituents.

The electronic and steric effects introduced by a conducting polymer's substituents can substantially change the polymer's conductivity. For example, in conducting polymers having heteroaromatic ring monomer units, the substituted five or six member heteroaromatic ring can be more conducting or less conducting than the unsubstituted parent heteroaromatic compound, depending upon electronic and steric effects.

III. Polyacetylene: Among The First Organic Conducting Polymers To Be Synthesized And Studied Polyacetylene is prepared chemically from acetylene by using an appropriate catalyst. As prepared chemically, polyacetylene is an insulator, exhibiting conductivities in the range of $10^{-10}$ to $10^{-13}$ S/cm (Siemens per centimeter) that correspond to the conductivity of known insulators, such as glass and DNA.

However, polyacetylene can be "doped" using a variety of oxidizing or reducing agents, such as antimony pentafluoride, the halogens, or aluminum chloride. By doping, polyacetylene is converted into a highly conducting polymer, exhibiting a conductivity of approximately $10^3$ S/cm, similar to the conductivity of metals such as bismuth. However, polyacetylene suffers from the drawbacks of extreme instability in air and a precipitous drop in conductivity whenever an acetylenic hydrogen is replaced by an alkyl or similar-type substituent group.

IV. Polypyrrole: Relatively Stable But A Precise Physical Structure Is Necessary To Provide Useful Conductivity Polypyrrole, a conducting polymer similar to polyacetylene, can be synthesized chemically or electrochemically and is more stable than polyacetylene. However, polypyrrole exhibits conductivity ranging from about 1 S/cm to about 100 S/cm and the conductivity can change dramatically, depending upon the precise composition and physical structure of the polypyrrole.

Alkyl groups on either the nitrogen or the carbons of the heteroaromatic pyrrole ring decreases the conductivity of polypyrrole. For example, an unsubstituted polypyrrole, incorporating the teterafluoroborate anion as the compensating counterion, exhibits a conductivity of 40 S/cm, whereas the N-methyl derivative, incorporating the same dopant, exhibits a conductivity of $10^{-3}$ S/cm; the 3-methyl derivative of pyrrole exhibits a conductivity of 4 S/cm; 3,4-dimethyl derivative has a conductivity of 10 S/cm; and the 3,4-diphenyl derivative exhibits a conductivity of $10^{-3}$ S/cm.

The conductivity decrease in substituted polypyrroles is attributed to several factors. First, the substituent introduced onto the heteroaromatic pyrrole ring cannot alter the oxidation potential of the parent heteroaromatic to the extent that electropolymerization at the anode is precluded. Secondly, the aromatic pi-electron system of the parent heterocycle must be maintained. Disruption of the pi-electron system of the heteroaromatic ring will adversely affect the relative stability of the aromatic and quinoid-like forms and therefore seriously reduce conductivity. A third critical consideration is that the functionality introduced onto the parent heterocycle must not create steric demands that preclude the adoption of a planar configuration by the conducting polymer.

This planar configuration requirement is significant. Numerous N-alkyl and N-aryl derivatives of polypyrrole have been prepared and discussed in the literature. However, even the simplest of these N-substituted polypyrroles, poly-N-methylpyrrole, exhibits conductivities that are three orders of magnitude lower than unsubstituted polypyrrole files doped with the same counterion. It is also possible to produce thin films of poly-N-aryl pyrroles, wherein the phenyl group is further substituted in the para position. However, polymers produced from these N-aryl pyrroles invariably exhibit conductivities three or more orders of magnitude less than the parent unsubstituted pyrrole. Such low conductivities preclude the use of these substituted polypyrroles in the development of analyte sensors.

The steric interaction introduced by the pyrrole ring substituents is important because of the mechanism of charge transport through the conducting polymer system. In one charge transport mechanism, electric charge is conducted through the polymer chain itself because of bipolaron structures that exist along the polymer chain. The bipolaron structures are defects occurring in the polymer lattice wherein two dopant counterions from the supporting electrolyte balance two positive centers found in the polymer.

Generally, the two positive centers are spaced, and confined, by approximately four monomer units and these defects serve to transport charge along the polymer chain. However, in order to transport charge along the chain, the compositions must be planar, such that the charge can be transported along the planar pi-electron system of the chain. If a substituent is sufficiently large, the steric interaction between constituents can distort the pyrrole monomer units out of planarity, thereby destroying the planarity of the pi-electron system, and destroying or seriously reducing the conductivity of the polymer.

Polymer substituents should not be strongly electron withdrawing or strongly electron-donating, as strong electronic effects can serve to destroy conductivity. However, especially for N-substituted pyrroles, the steric interactions, not electronic effects, are the main factor in determining polymerability, polymer conductivity and cyclic stability of the polymer between the doped and undoped state. Steric interactions in polypyrrole derivatives are more dominant because the predominant destabilizing interactions in pyrrole derivatives involve the hydrogen atom of the pyrrole nitrogen.

The synthesis and conductivities of polypyrrole and substituted polypyrroles have been extensively investigated as seen in the general references cited below. These references include the information discussed above and general information concerning the polypyrroles such as that the specific dopant can seriously affect the conductivity of the polymer; that conductivity is observed only for alpha-alpha coupling of monomers and not for alpha-beta coupling of monomers; and that polypyrrole films are stable, insoluble, and inert to most reagents, except possibly treatment by alkalis. The conductivity and stability of polypyrrole makes polypyrrole a good candidate for use in analyte sensors, if the polypyrrole conductivity can be maintained when functional groups are introduced onto the heteroaromatic ring.

The representative references discussing the polypyrroles include
G. Bidan, *Tet. Lett.*, 26(6):735-6 (1985).
P. Audebert, et al, *J. C. S. Chem. Comm.*, 887 (1986);
M. Wrighton, *Science*, 231:32 (1986);
R. Simon, et al., *J. Am. Chem. Soc.*, 104:2034 (1982);
Diaz, et al., *J. Electroanal. Chem.*, 133:233 (1982);
Saloma et al., *J. Electrochem. Soc.*, 132:2379 (1985);
Rosenthal, et al., *J. Electroanal. Chem. and Interfac. Chem.*, 1:297 (1985);
Bidan, et al., *Synth. Met.*, 15:51 (1986);
Salmon, et al., *J. Electrochem. Soc.*, 1897 (1985);
Genies et al., *Synth. Met.*, 10:27 (1984/85).
Bidan, et al., *Nouveau Jour. De Chimie*, 8:501 (1984);
Travers, et al., *Mol. Cryst. Liq. Cryst.*, 8:149 (1985).

V. Polythiophene: Relatively Stable But Also Requires Precise Physical Structure For Useful Conductivity Another well studied conducting polymer is polythiophene, wherein thiophene is electrochemically polymerized to yield a stable conducting polymer. Polythiophene resembles polypyrrole in that polythiophene can be cyclized between its conducting (oxidized) state and its nonconducting (neutral) state without significant chemical decomposition of the polymer and without appreciable degradation of the physical properties of the polymer. Polythiophene, like polypyrrole exhibits conductivity changes in response both to the amount of dopant and to the specific dopant, such as perchlorate, tetrafluoroborate, hexafluorophosphate, hydrogen sulfate, hexafluoroarsenate and trifluoromethylsulfonate.

Substituents placed on the heteroaromatic thiophene ring can affect the resulting conducting polymer. For example, thiophene polymerization can be affected by large substituents at the 3 and 4 positions, as seen in the inability of 3,4-dibromothiophene to polymerize. The electronic and steric effects introduced by the 3,4-dibromo substituents may prevent chain propagation. However, in contrast to pyrrole, ring substituents on thiophene do not seriously reduce the conductivity of the resulting heteroaromatic polymer.

The following are representative references concerning the synthesis and conductivity of polythiophene and substituted polythiophenes:
Tourillon, "Handbook of Conducting Polymers," Skotheim, ed., Marcel Dekker, Inc., New York, 1986, 293;
Waltham et al., *J. Phys. Chem.*, 87:1459 (1983);
Tourillon et al., *J. Polym. Sci. Polym. Phys. Ed.*, 22:33 (1984);
Tourillon et al., *J. Electroanal. Chem.*, 161:51 (1984);
Diaz et al., "Handbook of Conducting Polymers," Skotheim, ed., Marcel Dekker, Inc., New York 1986, p. 81.
Bargon, et al., *J. Res. Dev.*, 27:330 (1983);
Tourillon et al., *J. Phys. Chem.*, 87:2289 (1983); and Czerwinski, et al., *J. Electrochem. Soc.*, 2:2669 (1985).
Bryce, Chissil, Kathirgamanathan, Parker, and Smith, *J. C. S. Chem. Soc.*, 466 (1987).

The following references disclose the preparation and utility of internally doped (self-doped) conducting polymer films. These polymers may allow for highly ordered and therefore conductive films, as the potential counterions are covalently bound to the polymer backbone, instead of randomly diffused between polymer chains.

Patil, Ikenoue, Wudl, and Heeger, *J. Amer. Chem. Soc.*, 109:1858 (1987) discloses the preparation of sodium poly(3-thiophene-beta-ethanesulfonate) and sodium poly(3-thiophene-delta-butanesulfonate) internally doped films from their respective thiophene monomers.

Mager, Wudl, Patil, Ikenoue and Colaneri, 193, ACS National Meeting, April 5-10, 1987, Denver, Colo., Anal. Chem. Abstract #102 and Patil, et al., *Synthetic Metals*, 20:151 (1987) discloses self-doped conducting polymers.

VI. Poly[2,5-di(2-thienyl)-pyrrole]

McLeod, et al., *Polymer*, 27(3):455-8 (1986), discloses the synthesis and polymerization of functionalized 2,5-dithienylpyrrole (2,5-DTP) derivatives, including the electrochemical polymerization and the properties of the parent molecule, poly[2,5-di(2-thienyl)-pyrrole]. The primary objective of the McLeod article however was to determine the solubility of the polymer resulting from 2,5-DTP.

a. 2,5-DTP

The most common method of synthesizing 2,5-DTP is described in Wynberg and Metselaar, *Syn. Comm.*, 14:1 (1984). This method is illustrated below in TABLE 1.

c. 2,5-DTP Reactions

The 2,5-DTP monomer is a pyrrole having a thiophene group in the 2 and the 5 position, and therefore electrophilic substitution can occur at a number of positions along the thiophene groups or at the 1, 3, or 4 position of the pyrrole group.

The substitutent groups, pyrrole and thiophene, are heterocyclic compounds. Except for a general tendency to undergo addition reactions, these heterocycles do not

TABLE 1

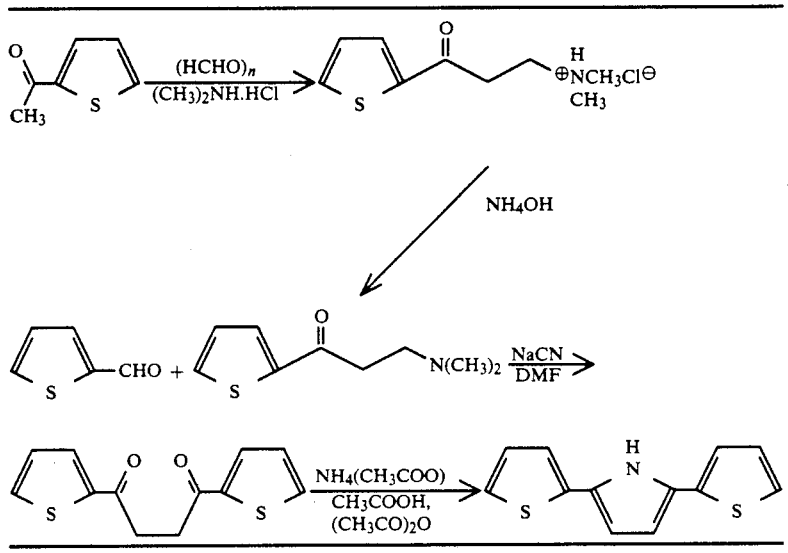

A modified version of this "Wynberg" method disclosing a method of preparing asymmetrical 2,5-dithienylpyrroles is shown in Phillips, Hebert, and Robichaud, *Syn. Comm.*, 16:411 (1986). However, the Phillips method, as well as the other methods identified below, are also rather complex, particularly in terms of large scale manufacturing.

Kooreman and Wynberg, *Recueil* 86:37 (1967) describes the synthesis of a terthienyl oligomer prepared using a Stevens rearrangement of N,N-di(thenoylmethyl)-N,N-dimethylammonium salt as a key step in the synthesis.

b. Electrophilic Substitution Reactions of Pyrroles and Thiophenes

Xu, Anderson, Gogan, Loader, and McDonald, *Tet. Lett.*, 22:4899 [1981] and Rokach, Hamel, Kakushima, and Smith, *Tet. Lett.*, 22:4901 (1981) disclose the use of N-benzenesulfonyl blocking groups to direct electrophilic substitution reactions of pyrrole to the 3-position.

Muchowski and Salas, *Tet. Lett.*, 24:3455 (1983), discloses the directing effect of the N-triisopropyl blocking group in the preparation of 3-substituted pyrrole derivatives.

Anderson and Loader, *Synthesis*, 353 (1985) summarizes conventional methodologies for the preparation of 3-substituted pyrroles from pyrrole.

The above identified references exemplify that the present state of the art is directed to electrophilic substituion reactions using N-1 pyrrole blocking groups to direct the reaction to the pyrrole C-3 position. Such a reaction scheme, however, requires additional manipulations and can be unduly complex and burdensome to manufacture on a large scale. Furthermore, such a reaction scheme often does not achieve optimal regioselectivity towards functionalization at the pyrrole 3-position.

have the properties expected of a conjugated diene or an amine or thioether. Thiophene does not undergo the oxidation typical of a sulfide, and pyrrole does not possess the basic properties typical of amines.

Instead, these heterocycles and their derivatives most commonly undergo electrophilic substitution: nitration, sulfonation, halogenation, Friedel-Crafts acylation, even the Reimer-Tiemann reaction and coupling with diazonium salts. For pyrrole, the nitrogen's extra pair of electrons (which is responsible for the usual basicity of nitrogen compounds) is involved in the pi electron cloud and is not available for sharing with acids. In contrast to most amines therefore pyrrole is an extremely weak base. By the same token, however, there is high electron density in the ring which causes pyrrole to be extremely reactive toward electrophilic substitution.

For thiophene, sulfur carries an unshared pair of electrons in a $sp^2$ orbital. The sulfur atom provides two electrons for the pi cloud and as a result is also extremely reactive toward electrophilic substitution.

OBJECTS OF THE INVENTION

It is an object of the present invention to functionalize the 2,5-DTP monomer to provide an oligomer which can be used to synthesize useful functionalized conducting organic polymers It is a further object of the present invention to provide a method of simply and efficiently functionalizing 2,5-DTP wherein the functional group is on the pyrrole ring and the resulting monomer can be polymerized into a useful conducting polymer.

It is a further object of the present invention to provide a method of simply and efficiently functionalizing 2,5-DTP monomer wherein the functional group is on the thiophene ring and the resulting monomer can be polymerized into a useful conducting polymer.

It is a further object of the present invention to provide a simple and easy method of synthesizing useful polymer intermediates based upon 2,5-DTP which in turn can be used to synthesize semi-conducting polymers.

It is a further object of the present invention to provide a simple regiospecific reaction scheme for synthesizing functionalized 2,5-DTP monomers wherein the functional group is placed at the 3 position It is a further object of the present invention to provide an electrophilic substitution reaction scheme for the regiospecific acylation on the thiophene portion of 2,5-DTP which in turn can be used to synthesize semiconducting polymers.

The electrophilic substitution reactions in this invention are accomplished under electrophilic reaction conditions which do not require the use of N-1 pyrrole blocking groups to direct reaction at the pyrrole C-3 position. This is because the steric bulk of the 2,5-dithienyl groups prevent N-acylation and therefore direct reactions with electrophiles on the pyrrole C-3 position.

The reaction conditions chosen have also demonstrated a greater regioselectivity towards functionalization at the pyrrole 3-position than the reaction conditions suggest in view of the prior art. This result can perhaps be explained by an activation of the pyrrole 3-position towards electrophilic substitution. This can arguably be attributed to an electron donating resonance contribution of the 2,5-thienyl groups as depicted below in TABLE 2.

TABLE 2

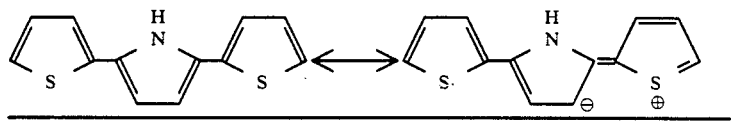

Other objects and features of the present invention will become obvious to those of ordinary skill in the art upon reading the following specification.

SUMMARY OF THE INVENTION

The present invention relates to a number of innovative electrophilic substitution reactions involving 2,5-dithienylpyrrole (2,5-DTP). These reactions are used in the synthesis of monomers for preparing functionalized conducting organic polymers. The electrophilic substitution reactions of this invention do not require the use of N-1 pyrrole blocking groups to direct the reaction at the preferred pyrrole C-3 position in one embodiment or to a thiophene group in another embodiment. The reactions chosen use electrophilic reaction conditions and have a greater regioselectivity towards functionalization than what is suggested in the prior art.

DETAILED DESCRIPTION OF THE PREFERRED EMBODIMENTS 2,5-DTP has been found to be a useful monomer which can be polymerized to yield a useful conducting polymer. It has also been found that functional groups can be placed at the C-3 position of the pyrrole to proved essentially the same high conductivity of the unsubstituted parent dithienylpyrrole. A variety of functional groups can be incorporated into the three-position of the pyrrole ring without adversely affecting the conductivity of the resulting polymer. As a result this monomer can be designed to carry any one of a number of functional groups, depending upon the type of conducting polymer desired. The monomer can then be polymerized and the resulting polymer will have a predictable and useful conductivity.

The present invention is directed to a number of innovative electrophilic substitution reactions involving 2,5-dithienylpyrrole (2,5-DTP). The reaction schemes of the present invention provide specialized monomers which in turn can be used in synthesizing useful, functionalized conducting organic polymers. The reaction schemes of this invention begin with the parent molecule 2,5-DTP which can be efficiently synthesized according to the procedures of Wynberg discussed above and illustrated in TABLE 1.

I. Synthesis of 3-(2-trifluoroacetamido)-methyl-2,5-DTP and 3-aminomethyl-2,5-DTP In U.S. Ser. No. 114,011, the compound 3-(2-trifluoroacetamido)-methyl-2,5-DTP was shown to be a useful oligomer for the preparation of functionalized conducting polymeric films. It has also been found that using unblocked 3-aminomethyl-2,5-DTP with hydrophobic counter ions and in protic solvents yields usable conducting polymers of improved stability in an aqueous environment. A key intermediate in the synthesis of both of these oligomers is 3-cyano-2,5-DTP. It was originally prepared in U.S. Ser. No. 114,011 using a multistep preparation featuring a base catalyzed cycloaddition reaction between acrylonitrile and N-(2-thienylmethyl)-2thienyliminochloride. The principal drawbacks of the procedure set forth in U.S. Ser. No. 114,011 are the number and complexity of the synthetic reactions required to make this product, which result in a low overall yield. In contrast, the following innovative reactive scheme has been developed to synthesize these compounds.

An electrophilic substitution reaction of 2,5-DTP has been surprisingly discovered whereby 2,5-DTP is reacted with chlorosulfonyl isocyanate (CSI) to produce 3-(N-chlorosulfonyl)-carboxamido-2,5-DTP, which need not be isolated and can be treated with dimethylformamide (DMF) to yield 3-cyano-2,5-DTP in 35% overall yield. The 3-cyano-2,5-DTP can be reacted with $B_2H_6$ and tetrahydrofuran (THF) to produce 3-aminomethyl-2,5-DTP in an overall yield of about 20%. By virtue of its ease and synthetic brevity, this process is clearly superior to most known procedures in the art. The reaction is illustrated in TABLE 3.

TABLE 3

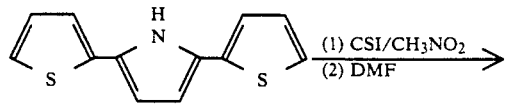

TABLE 3-continued

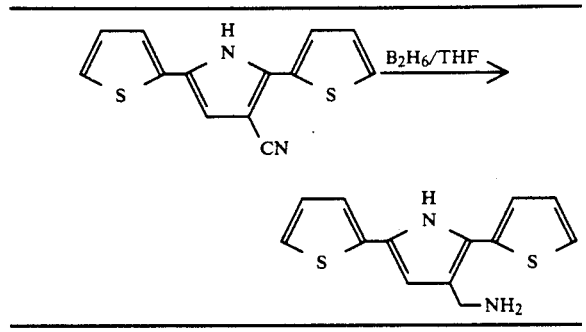

II. Synthesis of 3-formyl-2,5-DTP

Another innovative reaction scheme using the parent molecule 2,5-DTP involves an electrophilic substitution reaction of 2,5-DTP with either trimethylorthoformate in trifluoroacetic acid or with dimethylformamide and phosphorous oxychloride in 76–78% yields as depicted in TABLE 4.

TABLE 4

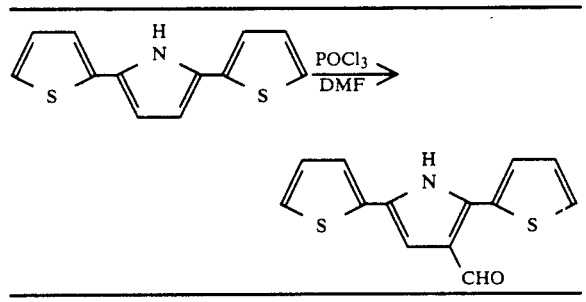

Condensation reactions of 3-formyl-2,5-DTP can be used to synthesize oligomers which in turn can be polymerized into useful conducting polymers. For example, to synthesize 3-carbomethoxyvinyl-2,5-DTP, the compound 3-formyl-2,5-DTP is reacted with methyl (triphenylphosphoranylidene)acetate. The resulting monomer can be polymerized into a conducting polymer film and this oligomer may be useful in increasing the detection of vibrational coupling energy of an analyte reaction due to its rigid side arm composition.

Other examples of 3-formyl-2,5-DTP condensation reactions with methylene compounds are provided below in TABLE 5.

TABLE 5

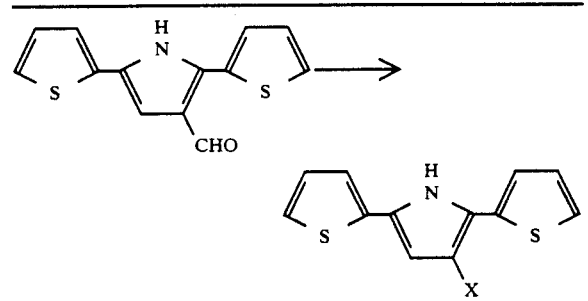

| Reagent | (X) |
|---|---|
| CH$_3$NO$_2$ | —CH=CH—NO$_2$ |
| (C$_6$H$_5$)$_3$P=CH—CO$_2$CH$_3$ | —CH=CH—CO$_2$CH$_3$ |
| CH$_3$SO$_3$CH$_3$, n-C$_4$H$_9$Li | —CHOHCH$_2$SO$_3$CH$_3$ |
| [(C$_6$H$_5$)$_3$PCH$_2$OCH$_3$]Br, n-C$_4$H$_9$Li | —CH$_2$CHO |
| LiCH$_2$CO$_2$-t-C$_4$H$_9$ | —CHOH—CH$_2$—CO$_2$t-C$_4$H$_9$ |

TABLE 5-continued

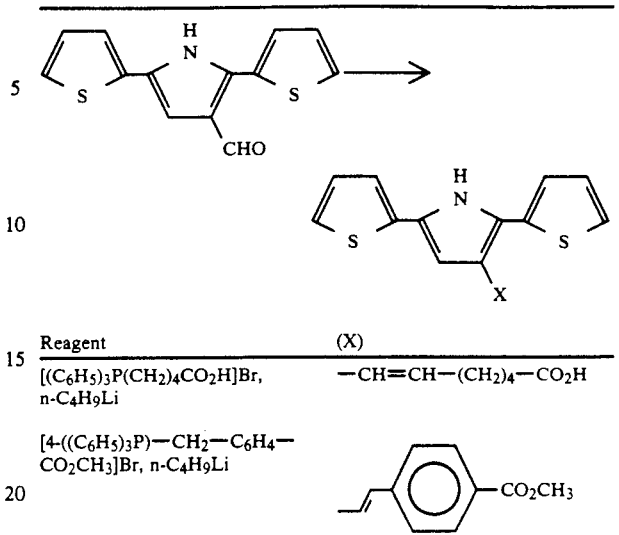

| Reagent | (X) |
|---|---|
| [(C$_6$H$_5$)$_3$P(CH$_2$)$_4$CO$_2$H]Br, n-C$_4$H$_9$Li | —CH=CH—(CH$_2$)$_4$—CO$_2$H |
| [4-((C$_6$H$_5$)$_3$P)—CH$_2$—C$_6$H$_4$—CO$_2$CH$_3$]Br, n-C$_4$H$_9$Li | (phenyl-CO$_2$CH$_3$ group) |

The aldol condensation of 2,5-DTP with the lithium salt of methyl methanesulfonate, as disclosed in the above TABLE 5, provides an oligomer that may be of particular usefulness in the synthesis of polymers with intramolecularly bound anionic dopants (self doped polymers).

III. Electrophilic substitution of 2,5-dithienyl-pyrrole with iminium salt derivatives.

An innovative facile electrophilic substitution reaction of DTP with polyformaldehyde and amines has also been discovered. This reaction can be used to synthesis new oligomers such as those summarized below in TABLE 6.

TABLE 6

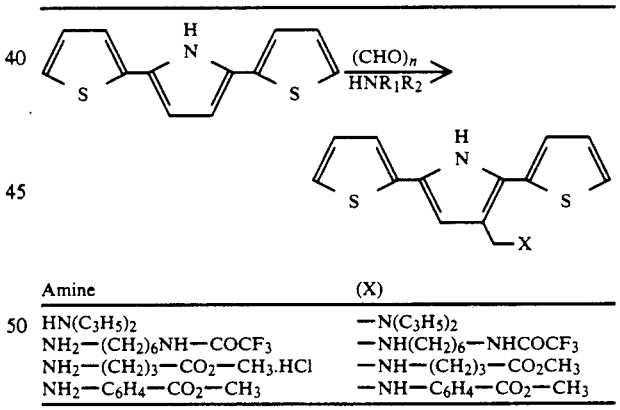

| Amine | (X) |
|---|---|
| HN(C$_3$H$_5$)$_2$ | —N(C$_3$H$_5$)$_2$ |
| NH$_2$—(CH$_2$)$_6$NH—COCF$_3$ | —NH(CH$_2$)$_6$—NHCOCF$_3$ |
| NH$_2$—(CH$_2$)$_3$—CO$_2$—CH$_3$.HCl | —NH—(CH$_2$)$_3$—CO$_2$CH$_3$ |
| NH$_2$—C$_6$H$_4$—CO$_2$—CH$_3$ | —NH—C$_6$H$_4$—CO$_2$—CH$_3$ |

An alternative approach to the synthesis of these N-functionalized aminomethyl DTP derivatives would be in the initial formation of the Schiff base imines of the spacer arms with 3-formyl-2,5-DTP, followed by their reduction under standard conditions, as shown below in TABLE 7.

TABLE 7

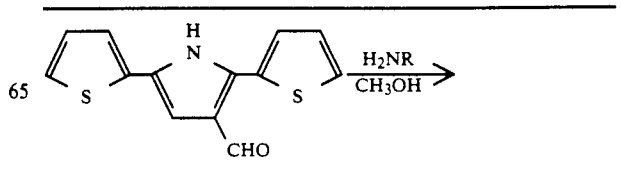

TABLE 7-continued

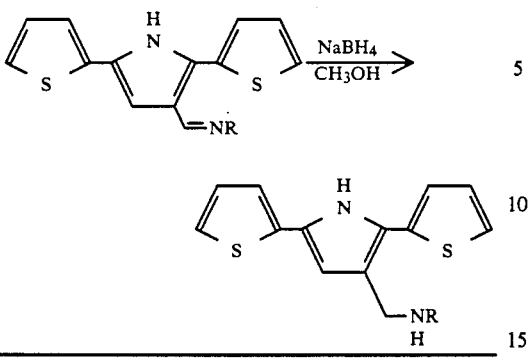

IV. Synthesis of 3-N-trifluoroacetamidoethyl-2,5-DTP

The monomer 3-N-trifluoroacetamidoethyl-2,5-DTP has been found to provide polymer films of useful conductivity. The reaction scheme is shown in TABLE 8, wherein 3-formyl-2,5DTP is combined with nitromethane to cause a condensation reaction to produce 3-nitrovinyl-2,5-DTP. Subsequent reduction and trifluoroacetylation produced 3-N-trifluoroacetamidoethyl-2,5DTP in 45% overall yield.

TABLE 8

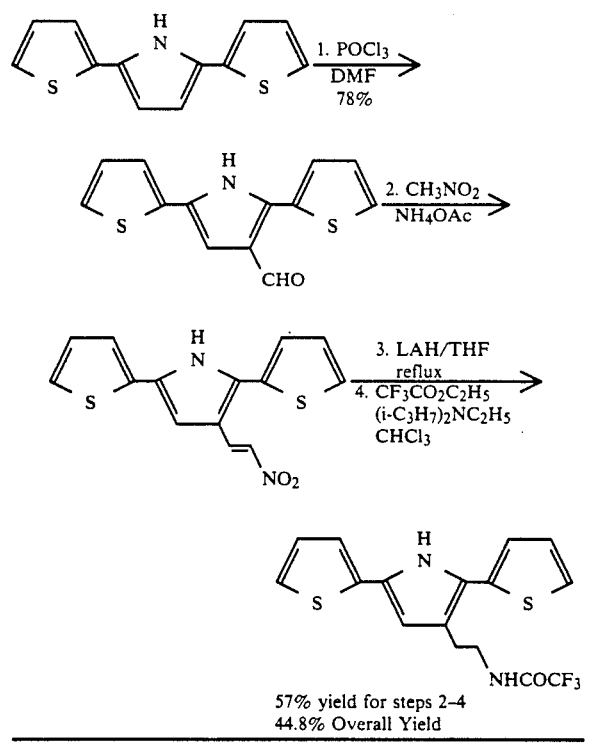

57% yield for steps 2-4
44.8% Overall Yield

V. Synthesis Of Other Electrophilic Substitution Reactions Of 2,5-Dithienylpyrrole In addition to electrophilic substitution reactions of 2,5-DTP with N-bromosuccinimide, chlorosulfonyl isocyanate, trimethyl orthoformate, dimethylformamide with phosphorous oxychloride, iminium salts, and acetyl chloride, other possible electrophiles can be used such as is shown in TABLE 9.

TABLE 9

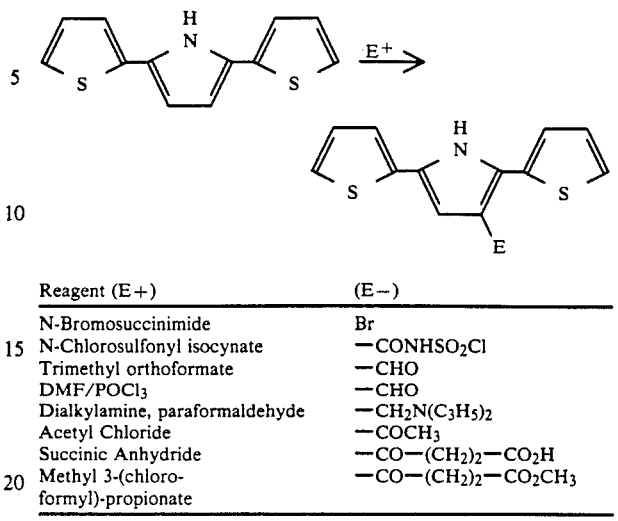

| Reagent (E+) | (E−) |
|---|---|
| N-Bromosuccinimide | Br |
| N-Chlorosulfonyl isocynate | —CONHSO$_2$Cl |
| Trimethyl orthoformate | —CHO |
| DMF/POCl$_3$ | —CHO |
| Dialkylamine, paraformaldehyde | —CH$_2$N(C$_3$H$_5$)$_2$ |
| Acetyl Chloride | —COCH$_3$ |
| Succinic Anhydride | —CO—(CH$_2$)$_2$—CO$_2$H |
| Methyl 3-(chloro-formyl)-propionate | —CO—(CH$_2$)$_2$—CO$_2$CH$_3$ |

VI. Examples

EXAMPLE 1

Preparation of 3-Cyano-2,5-Dithienylpyrrole (3)

To a stirred solution of 2,5-dithienylpyrrole (105 mg, 0.45 mmol) in dry acetonitrile (1.6 mL) was added chlorosulphonyl isocyanate (39.5 μL, 0.45 mmol) in acetonitrile (0.16 mL) over a period of 10 minutes with stirring at 0°-5° C. (ice bath). The reaction mixture was stirred for 30 minutes and then dry dimethylformaide (35 mg) in acetonitrile (1.6 mL) was added. After stirring for 3 hours at 0°-5° C., the reaction mixture was poured into water and extracted three times with chloroform (50 mL). The chloroform extract was dried with anhydrous magnesium sulfate and the solvent removed under vacuo. The residue was charged on a column of silica gel (50 g) and eluted with toluene-tetrahydrofuran, 19:1, to furnish a greyish-yellow solid (69 mg, 58%); m.p. 202°-203° C.

IR (KBr): 3210, 3160, 2210 cm$^{-1}$.

NMR (60 MHz, DMSO-d$_6$): δ6.94-7.73 (m, 7H); 6.56 (d, 1H, J=3 Hz, C-4 pyrrole-H).

Mass Spectrum (EI) m/e: 256.3 (M+, 100%).

Analysis: Calculated for C$_{13}$H$_8$N$_2$S$_2$: 60.91; H, 3.15; N, 10.93.

Found: C, 61.16; H, 3.26; N, 11.06.

EXAMPLE 2

Preparation of 3-Formyl-2,5-Dithienylpyrrole (5)

Phosphorus oxychloride (0.11 mL) was added dropwise with stirring at room temperature to dimethylformamide (0.5 mL). A solution of dithienylpyrrole (250 mg, 1.08 mmol) in dimethylformaide (0.3 mL) was then added gradually at 20°-30° C. The solution was then kept at 35°-37° C. for 45 minutes and finally then poured into stirred ice (1 g) and water (1 mL). Sodium hydroxide (0.19 g) in water (1 mL) was added over a period of ½ hour at room temperature, the rate of addition being such that when ca. ¾ of sodium hydroxide solution had been added the mixture was at pH 6.0. The remainder was then added at once. Water (2 mL) was then added and the mixture boiled for 3 minutes. The resultant aldehyde, which now smelled strongly of dimethylamine, was cooled in ice and the yellow colored granular precipitate filtered off and washed successively with water (175 mL) and ice cold ether (80 mL) to remove brown impurity. The aldehyde was dried at 80° C. Recrystallization from ethanol gave a yellow solid (217 mg, 78%.

m.p. 264°-266° C.

IR (KBr): 3450, 3230, 2830, 1640, 1470, 1380, 1330, 1240, 1180, 1060, 820, 780, 690 cm$^{-1}$.

NMR (60 MHz, DMSO-d$_6$,): δ 9.97 (s, 1H, —CHO), 6.90-7.63 (m, 2H), 6.63 (s, 1H, C-4 pyrrole-H).

Mass spectrum (EI) m/e: 259.1 (M+, 100%).

Analysis: Calculated for $C_{13}H_9NOS_2$: C, 60.20; H, 3.50; N, 5.40.

Found: C, 60.27; H, 3.58; N, 5.29.

EXAMPLE 3

Preparation of 3-(2'-Carbomethoxyvinyl)-2,5-Dithienylpyrrole (8)

To a solution of 100 mg (0.386 mmole) of 3-formyl-2,5-dithienylpyrrole in toluene (3 mL) was added methyl (triphenylphosphoranylidene)acetate (129 mg, 0.386 mmol) at room temperature. The reaction mixture was then stirred at 60° C. for 16 hours. The reaction solvent was evaporated under reduced pressure, and the crude product then purified on 50 g of silica gel. Elution with hexane-ethyl acetate, 5:1, gave the title compound (97 mg) in 58% yield.

Rf: 0.20 (hexane-ethyl acetate, 3:1).

NMR (60 MHz, DMSO-d$_6$) δ 7.90 (d, 1H, J=16 Hz, CH=C), 6.90-7.53 (m, 6H), 6.63 (d, 1H, J=2H$_2$, pyrrole C4-H), 6.16 (d, 1H, J=16 Hz, CH=C), 3.76 (s, 3H, —CO$_2$Me).

IR (KBr): 3400, 1675, 1615, 1510, 1460, 1430, 1280, 1255, 1030, 970, 785, 690 cm$^{-1}$.

Mass Spectrum (EI) m/e: 315.1 (M+, 100%).

EXAMPLE 4

Preparation of 3-(2'-Hydroxy-1'-Methylsulfonylethyl)2,5-Dithienylpyrrole (9)

The lithio derivative of methyl methanesulfonate was prepared at −78° C. under argon by the dropwise addition of 0.56 mL of a 1.60M n-butyllithium (0.891 mmol) to a solution of 72 μL (0.85 mmol) of methyl methanesulfonate in 2 mL of anhydrous tetrahydrofuran. After 45 minutes at −78° C., 3-formyl-2,5-dithienylpyrrole (105 mg, 0.41 mmol) in 1 mL of tetrahydrofuran was added dropwise over a 5 minute period to the lithio methyl methanesulfonate solution. The reaction mixture was allowed to stir for 30 minutes at −78° C. After the completion of reaction, it was then quenched with a saturated aqueous ammonium chloride solution. The aqueous layer was extracted three times with 50 mL portions of ethyl acetate and the combined organic layers were washed with water (10 mL×1) and brine (10 mL×1). The organic layer was dried over anhydrous magnesium sulfate, filtered and the solvent was removed under reduced pressure. The crude product was purified on 50 g of silica gel. Elution with hexane-ethyl acetate (5:1), gave 64 mg (43%) of title compound.

Rf: 0.31 (hexane-ethylacetate, 3:1).

NMR (60 MHz, CD$_3$OD) δ 6.80-7.46 (m, 6H), 6.33-6.60 (brs, 1H, pyrrole C4-H), 3.90 (s, 3H, SO$_3$Me), 3.50-3.76 (m, 2H, CH$_2$—SO$_3$—), 3.26-3.43 (m, 1H, CH—OH).

IR (CHCl$_3$) 3549, 3445, 3367, 3008, 2959, 1650, 1509, 1456, 1423, 1359, 1252, 1177, 1083, 1041, 999, 972, 846, 810, 700, 662 cm$^{-1}$.

EXAMPLE 5

Preparation of 3-(2-Aminoethyl)-2,5-Dithienylpyrrole

A solution of 3-formyl-2,5-dithienylpyrrole (100 mg, 0.83 mmol) in nitromethane (1 mL) containing ammonium acetate (21.9 mg, 0.38 mmol) was refluxed for 45 minutes. The solvent was evaporated under reduced pressure, and the residue was then dissolved in 50 mL of ethyl acetate. The organic phase was washed with water (10 mL), brine (10 mL×2) and dried over anhydrous magnesium sulfate. Evaporation of solvent in vacuo gave a crude material (127 mg) which without further purification was used directly for next reaction.

Rf: 0.28 (hexane-ethyl acetate, 3:1).

NMR (60 MHz, CDDCl$_3$): δ 8.2 (d, 1H, J=13 Hz, CH=C), 7.40 (d, 1H, J=13 Hz, C=CH—), 6.90-7.60 (m, 7H), 6.56 (d, 1H, J=2 Hz).

A solution of crude 3-(2'-nitrovinyl)-2,5-dithienylpyrrole (127 mg) in pure dry tetrahydrofuran (1.5 mL) was added with stirring to a suspension of lithium aluminum hydride (47 mg, 1.23 mmol) in boiling tetrahydrofuran (2 mL) at a rate sufficient to maintain reflux. The mixture was refluxed for 35 minutes, then cooled, and the excess of hydride decomposed by successive addition of 50 μL of H$_2$O, 50 μL of 40% aqueous sodium hydroxide solution and 150 μL of water. The reaction mixture was allowed to stir at room temperature for one hour. The resultant suspension was then filtered through a pad of anhydrous magnesium sulfate and the filter cake washed four times with ethyl acetate (50 mL). The combined filtrate was evaporated under reduced pressure, leaving a straw-colored solid. This solid was then purified on 50 g of silica gel. Elution with methanol: chloroform:ammonium hydroxide, 1:20:0.1, gave 75 mg (82%, 2 steps) of 3-aminoethyl-2,5-dithienyl pyrrole.

Rf: 0.16 (chloroform:methanol:ammonium hydroxide, 12:1:0.1).

NMR (60 MHz, CDCl$_3$): δ 6.8-7.4 (m, 6H), 6.30 (s, 1H), 2.80 (m, 4H), 2.0 (m, 2H, —NH$_2$).

IR (CHCl$_3$): 3430, 2920, 1590, 1520, 1430, 1270 cm$^{-1}$.

Mass Spectrum (EI) m/e: 274.0 (M$^{30}$, 35%).

EXAMPLE 6

3-Diallylaminomethyl-2,5-Dithienylpyrrole

Paraformaldehyde (9.1 mg, 0.3 mmol) was added to a solution of acetic acid (0.33 mL, 0.71 mmol) and diallylamine (0.32 mmol) in 1 mL of ethanol. After stirring at room temperature for a few minutes, 2.5-dithienylpyrrole (0.3 mmol) was then added all at once. The reaction mixture was then allowed to stir at 60° for 19 hours. The reaction solvent was evaporated under reduced pressure, and the crude product was taken up with ethyl acetate. The organic layer was then washed with water (10 mL) and brine (10 mL). The aqueous layer was extracted with chloroform (10 mL). The combined organic layers were then dried over anhydrous magnesium sulfate, filtered and the solvent was removed under pressure. The crude product was purified on 50 g of silica gel. Elution with hexane-ethyl acetate (5:1), gave 67 mg (65%) of title compound.

Rf: 0.16 (hexane-ethyl acetate, 5:1).

NMR (60 MHz, CDCl$_3$): δ 6.90-7.26 (m, 6H, protons on thiophene), 6.30-6.63 (3H, olefinic proton and proton on pyrrole), 5.56-6.16 (m, 2H, olefinic H), 5.00-5.40 (m, 2H, —CH=CH$_2$), 3.60 (s, 2H, —CH$_2$—N—), 3.20 (s, 2H —N—CH$_2$—), 3.20 (s, 2H, —N—CH$_2$—).

30 Mass Spectrum (EI) m/e: 340.2 (M+, 22.5%), 244 (M+—N(C₃H₅)₂, 100%.

EXAMPLE 7

Preparation of 3-Acetyl-2,5-Dithienylpyrrole

Acetic anhydride (75 µL, 1.75 mmol) was dissolved in 2 mL of anhydrous methylene chloride and stirred for 2 minutes at 0° C. under nitrogen. To this stirred mixture was added boron trifluoride etherate (185 µL, 1.5 mmol), followed by the addition of 1.5 mmol 2,5-dithienylpyrrole in 1 mL of anhydrous methylene chloride. The resultant dark green solution was stirred at 0° C. for 15 minutes and room temperature for 1 hour. The solution was diluted with chloroform (50 mL) and washed four times with water (10 mL), twice with saturated sodium bicarbonate (10 mL), and finally twice with water (10 mL). The organic phase was evaporated and the residue was chromatographed on a silica gel column (50 g). Elution with 30% ethyl acetane in hexane gave 93 mg (68%) of 3-acetyl-2,5-dithienylpyrrole.

Rf: 0.40 (hexane-ethyl acetate=3.1).

NMR (60 MHz, CDCl₃) δ 7.46 (dd, 1H, J=4 Hz, 2 Hz), 6.83-7.36 (m, 6H), 6.70 (d, 1H, J=3 Hz), 2.36 (s, 3H, CH₃—CO).

IR (CHCl₃): 3618, 3440, 3009, 1662, 1478, 1448, 1421, 1252, 1048, 921, 879, 848, 701 cm⁻¹.

Mass Spectrum (EI) m/e, 273.0 (M+, 76.9%), 258 (M+—CH₃, 100%).

EXAMPLE 8

Preparation of 3-Bromo-2,5-Dithienylpyrrole

To a solution of 2,5-dithienylpyrrole (130 mg, 0.56 mmol) in 2.5 mL of anhydrous tetrahydrofuran cooled to −78° C. was added N-bromosuccinimide (99.68 mg, 0.56 mmol). After addition was complete the cooling bath was removed and the reaction mixture was allowed to stand in a −20° C. freezer for 4 hours, during which the solution became a brown color. The reaction mixture was concentrated under reduced pressure, carbon tetrachloride was added to precipitate the succinimide, and this mixture was filtered. The filter cake was washed with additional chloroform, the combined filtrates were concentrated, and the resulting oil was chromatographed on silica gel (50 g). Elution with hexane-ethyl acetate, 4:1, furnished 81 mg (46%) of 3-bromo-2,5-dithienylpyrrole.

Rf: 0.50 (hexane-ethyl acetate, 3:1).

NMR (60 MHz, CDCl₃) δ 6.80-7.30 (m, 6H), 6.37 (d, 1H, J=3 Hz).

IR (KBr) 3450, 1630, 1500, 1270, 780, 690 cm⁻¹.

Mass Spectrum (EI) m/e: 309 (M+, 67.4%), 311 (M+ +2, 67.7%).

VII. Obtaining Regioselectivity By Varying The Amount Of Catalyst

Another preferred reaction scheme of the present invention is directed to the following equation:

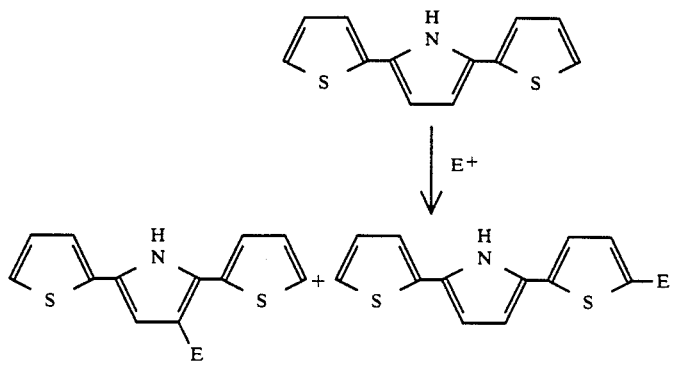

where E is any electrophile. Placing such a functional group upon the 3 carbon pyrrole of 2,5-DTP has been found to provide a monomer which can be polymerized into a polymer of useful conductivity. Such a functional group may also be placed on the thiophene portion to also provide a monomer which can be polymerized into a polymer of useful conductivity. Of these two possible placements of the functional group, the most preferred will depend upon the precise functional group being used and the conductivity desired.

It has been surprisingly found that the functional group (R—C=O) can be selectively bonded onto the pyrrole group or the thiophene group of 2,5-DTP, depending upon the amount of AlCl₃ catalyst used in the reaction. If about one equivalent of catalyst is used per equivalent of

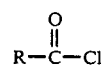

the pyrrole portion of 2,5-DTP will be functionalized (at the 3 position). If about four equivalents of catalyst and two equivalents of acid chloride are used, both the thiophene and pyrrole will be functionalized in about equal amounts. Finally, if about six equivalents of catalyst and three equivalents of acid chloride are employed, the substitution will occur principally upon the thiophene group.

EXAMPLE 9

Methyl 4-{2'-thienyl-5'-[2''-pyrrolyl-5''-(2'''-thienyl)]}-4-oxobutyrate

About 400 mg (3 mmole) of AlCl₃ were suspended in 4 ml of anhydrous methylene chloride. About 184 microliters (1.5 mmole) of 3-carbomethoxypropionyl chloride were added at 0° C to the suspension. After stirring for 10 minutes, a solution of 2,5-DTP (11.6 mg, 0.5 mmole) in 2 ml of anhydrous methylene chloride was added. The mixture was stirred at 25° C. for 1 hour. The reaction mixture was poured into ice and water, neutralized with 1N HCl solution, and the organic layer collected. The aqueous layer was extracted 3 times with 20 ml portions of ethyl acetate and the combined organic layer was washed with water thoroughly, dried over anhydrous magnesium sulfate, and concentrated under reduced pressure to give dark green oil. The oil was then purified on 100 grams of silica gel eluted with hexane-ethyl acetate (3:1 to 2:1) thereby providing 73 mg (43%) title compound.

Rf: 0.48 (hexane-ethyl acetate, 3:1) IR (KBr) 1730, 1655, 1630, 1475, 1438, 1255, 1225, 1160, 1090, 1045, 780 cm$^{-1}$.

NMR (300 Hz CDCl$_3$) 8.57 (brs, 1H, N-H), 7.65 (d, 1H. J=4.05 Hz. C3-H), 7.21 (dd. 1H, J=5.07 Hz, 1.03 Hz, C2″-H), 7.15 (d,1H, J=4.6 Hz, C4″-H), 7.08 (d, 1H, J=3.96 Hz, C4-H), 7.05 (dd, 1H, J=5.0 Hz, 4.84 Hz; C3″-H), 6.60 (m, 1H, proton on pyrrole), 6.46 (dd, 1H, J=3.70 Hz, 2.50 Hz; proton on pyrrole), 3.69 (S, 3H, —CO$_2$Me), 3.22 (t, 2H, J=7.0 Hz, CH$_2$—CH$_2$), 2.76 (t, 2H, J=7.0 Hz, —CH$_2$—CH$_2$).

$^{13}$C NMR (300 MHz), CDCl$_3$): δ 190.4 (CO), 173.4 (CO), 144.1 (Cq), 139.3 (Cq), 134.9 (Cq) 133.3, 129.4 (Cq), 127.8 (CH), 126.5 (Cq), 123.6 (CH), 122.0 (CH), 121.2 (CH), 110.9 (CH), 109.1 (CH), 51.9 (CH$_3$), 33.4 (CH$_2$) 28.2 (CH$_2$)

Mass Spectrum (E1): m/e 345.1 (M+, 100%).

EXAMPLE 10

Methyl 4-{2′-Thienyl-5′-[2″-Pyrrolyl-3″-(4-Carbomethoxy-1-Oxopropyl)-5″-(2′″-Thienyl)]}-4-Oxobutyrate and Methyl 4-{2′-Thienyl-5′-[2″-Pyrrolyl-5″-(2′″-Thienyl)]}-4-Oxobutyrate To a suspension of AlCl$_3$ (266.7 mg, 2.0 mmol) in 4 mL of anhydrous methylene chloride was added dropwise 3-carbomethoxypropionyl chloride (123 μL, 1.0 mmol) at 0° C. The resultant solution was stirred for 10 minutes, a solution of 2.5-dithienyl pyrrole (116 mg, 0.5 mmol) in 2 mL of anhydrous methylene chloride was added, and the mixture was stirred at 25° C. for one hour. The reaction mixture was poured into ice and water, neutralized with 2N H$_2$SO$_4$ solution, and the organic layer collected. The aqueous layer was extracted with ethyl acetate (30 mL×3), and the combined organic layers were dried over anhydrous magnesium sulfate. Filtration and concentration under reduced pressure provided a dark green oil. It was then purified on 100 g of silica gel. Elution with hexane-ethyl acetate (3:1 to 1:1) gave 92.3 mg (40%) of disubstituted compound and 30 mg (17%) of monosubstituted compound. Disubstituted product possesses the physical properties shown as follows:

Rf: 0.19 (hexane-ethyl acetate, 1:1).

IR (CHCl$_3$) 3733, 3694, 3650, 3520, 3437, 3293, 3018, 2851, 2352, 1997, 1734, 1660, 1589, 1537, 1515, 1479, 1435, 1358, 1325, 1299, 1208, 1171, 1684, 996, 909, 850, 803, 707, 660 cm$^{-1}$.

NMR (300 MHz, CDCl$_3$): δ 9.18 (brs, 1H, —NH), 7.61-2.64 (m, 2H), 7.39 (dd, 1H, J=5.1 Hz, 1.0 Hz, proton on thiophene), 7.15 (d, 1H, J=4.0 Hz), 7.09 dd, 1H, J=5.0 Hz, 3.72 Hz), 6.97 (d, 1H, J=2.78 Hz, proton on pyrrole ring), 3.70 (s, 3H, —CO$_2$Me), 3.68 s, 3H, —CO$_2$Me), 3.20 (t, 2H, J=6.72 Hz), 3.12 (t, 2H, J=6.70 Hz, —CH$_2$—CH$_2$—), 2.75 (t, 3H, J=6.70 Hz, —CH$_2$—CH$_2$—)), 2.71 (t, 2H, J=6.70 Hz, —CH$_2$—CH$_2$—).

$^{13}$C NMR (300 MHz, CDCl$_3$) 193.5 (CO), 190.5 (CO) 173.8 (CO), 173.4 (CO), 142 4 (Cq), 140.5 (Cq), 133.1 (CH), 132.0 (Cq), 131.4 (Cq), 128.3 (CH), 127.2 (CH), 122.7 (CH), 125.9 (Cq), 122.7 (CH) 122.1 (Cq), 110.9 (CH), 51.9 (CH$_3$), 51.8 (CH$_3$), 35.1 (CH$_2$), 33.3 (CH$_2$), 27.93 (CH$_2$), 27.90 (CH$_2$).

Mass Spectrum (EI) m/e: 459.1 (M+, 100%).

More substituted compound possesses the following physical properties.

Rf: 0.48 (hexane-ethyl acetate, 3:1).

IR (KBr) 1730, 1655, 1630, 1475, 1438, 1255, 1225, 1160, 1090, 1045, 780 cm$^{-1}$.

NMR (300 MHz, CDCl$_3$) δ 8.57 (brs, 1H, —NH), 7.65 (d, 1H, J=4.05 Hz, C3-H), 7.21 (dd, 1H, J=5.07 Hz, 1.03 Hz, C2″-H), 7.15 (d, 1H, J=4.6 Hz, C4″-H), 7.08 (d, 1H, J=3.96 Hz), 7.05 (dd, 1H, J=5.0 Hz, 4.84 Hz, C3″-H), 6.60 (m, 1H, proton on pyrrole), 6.46 dd, 1H, J=3.70 Hz, 2.50 Hz, proton on pyrrole), 3.69 (s, 3H, —CO$_2$Me), 3.22 (t, 2H, J=7.0 Hz, —CH$_2$—CH$_2$—), 2.76 (t, 2H, J=7.0 Hz, —CH$_2$—CH$_2$—).

$^{13}$C NMR (300 MHz, CDCl$_3$) δ 190.4 (CO), 173.4 (Cq), 139.3 (Cq), 134.9 (Cq), 133.3 (CH), 129.4 (Cq), 127.8 (CH), 126.5 (Cq), 123.6 (CH), 122.0 (CH), 121.2 (CH), 110.9 (CH), 109.1 (CH), 51.9 (CH≧3° ), 33.4 (CH$_2$, 28.2 (CH$_2$).

Mass Spectrum (EI) m/e: 345.1 (M+, 100%).

EXAMPLE 11

While polymers may be formed from a wide variety of electrolytes for comparison purposes the following system was employed. Films were formed by combining 50 mM tetraethylammonium para-toluene sulfonate and 5 mM dithienylpyrrole monomer in acetonitrile. The resulting liquid was deposited on gold coated glass slides by applying 0.35 V using a Ag/AgCl reference with a Pt cathode. The amount of charge passed during electropolymerization was monitored and the thickness of the films was calculated based on the total charge consumed. Polymers were also deposited on gold microelectrode interdigitated finger "devices" by application of a constant current of 20 μA for 100 sec. to yield 2000 A films which bridge the gap between fingers.

Conductivity Measurement:

Films were removed from the gold by coating with UV curable epoxy and immersing in gold etchant. Conductivity of the films was measured by a standard four-point probe technique. Resistance of the devices was measured and the polymer's conductivity calculated based on the known geometry of the electrode pattern.

Results:

The following are results for conductivity measurements of the polymers A and B.

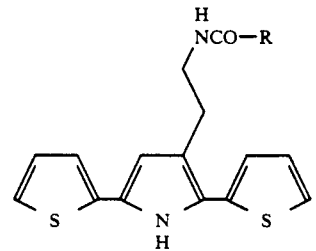

where R is (A) (CH$_2$)$_2$CO$_2$CH$_3$

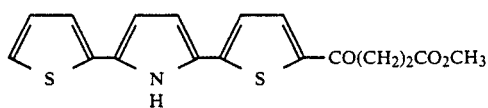

| DEVICE | FILM $(ohm\cdot cm)^{-1}$ | DEVICE (Kohms) | APPROXIMATE CALCULATED CONDUCTIVITY $(\Omega\text{-cm}^-)$ |
| --- | --- | --- | --- |
| A |  | 40–60 | $5 \times 10^{-4}$ |
| B | $1\text{–}3 \times 10^{-3}$ | 25 | $1 \times 10^{-3}$ |

The present invention is defined by the claims which are provided below, and the present discussion is merely provided to help understand the claims and understand the numerous possible embodiments of the present invention as defined by the claims. The limitations defining this invention are expressly outlined in the claims, and nothing provided in this discussion is intended to provide any additional limitation thereto.

What is claimed is:

1. The compound

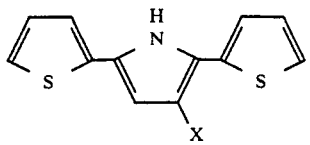

in which X is —CHO, —CH═CH—NO$_2$, —CH═CH—CO$_2$CH$_3$, —CHOHCH$_2$SO$_3$CH$_3$, —CHOH—CH$_2$—CO$_2$t—C$_4$H$_9$, —CH═CH—(CH$_2$)$_4$—CO$_2$H,

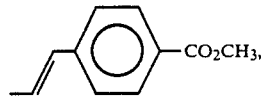

—N(C$_3$H$_5$)$_2$, —NH(CH$_2$)$_6$—NHCOCF$_3$, —NH—(CH$_2$)$_3$—CO$_2$CH$_3$, —NH—C$_6$H$_4$—CO$_2$—CH$_3$, —(CH$_2$)$_2$—NHCOCF$_3$, —Br, —CONHSO$_2$Cl, —CHO, —CH$_2$N(C$_3$H$_5$)$_2$, —COCH$_3$, —CO(CH$_2$)$_2$CO$_2$H or —CO(CH$_2$)$_2$CO$_2$CH$_3$.

2. Methyl 4-{2'-thienyl-5'-{2''-pyrrolyl-5''-(2'''-thienyl)]}-4-oxobutyrate.

* * * * *

UNITED STATES PATENT AND TRADEMARK OFFICE
CERTIFICATE OF CORRECTION

PATENT NO. : 5,021,586

DATED : June 4, 1991

INVENTOR(S) : James P. Albarella and Nan-Horng Lin

It is certified that error appears in the above-identified patent and that said Letters Patent is hereby corrected as shown below:

Column 1, line 17; change "4,886,623" to ---4,886,625---.

Column 2, line 64; change "files" to ---films---.

Column 3, line 56; insert a colon (:) after include.

Column 4, line 1; change "cryst. 8:149" to ---cryst., $\underline{118}$:149---.

Column 4, line 43; change "Soc., 2:2669(1985)" to ---132:2669(1985)---.

Column 5, line 48; change "[1981)" to ---(1981)---.

Column 10, lines 1-14; delete the equation since it is included twice in Table 5.

Column 12, line 14; change "Br" to --- -Br ---.

Column 12, line 46; change "$C_{13}H_8N_2S_2$: 60:91;" to ---$C_{13}H_8N_2S_2$: C, 60.91;---.

Column 13, line 4; change "78%." to ---78%).

Column 13, line 66; change "IR(CHCl$_3$)3549," to ---IR(CHCl$_3$):3549,---.

Column 14, lines 12-13; change "in vacuuo" to ---$\underline{in\ vacuuo}$---.

Column 14, line 42; change "($M^{30}$, 35%)." to ---($M^+$, 35%).---.

Column 14, line 67; change "-CH=CH$_2$), 3.60" to --- -CH=C$\underline{H}_2$), 3.60 ---.

Column 14, line 67; change "(s,2H,-CH$_2$-N-)," to ---(s,2H,-C$\underline{H}_2$-N-),---.

Column 14, line 68; change "(s,2H-N-CH$_2$-), 3.20 (s,2H,-N-CH$_2$)." to ---(s,2H-N-C$\underline{H}_2$-), 3.20 (s,2H,-N-C$\underline{H}_2$-).---

Column 15, line 1; change "30 Mass Spectrum" to ---Mass Spectrum---.

Column 15, line 66; change "CDCl$_3$ $\delta$ 6.80-7.30" to ---CDCl$_3$:$\delta$ 6.80-7.30---.

Column 17, line 9; change "CDCl$_3$) 8.57" to ---CDCl$_3$:8.57---.

UNITED STATES PATENT AND TRADEMARK OFFICE
CERTIFICATE OF CORRECTION

PATENT NO. : 5,021,586

DATED : June 4, 1991

INVENTOR(S) : James P. Albarella and Nan-Horng Lin

It is certified that error appears in the above-identified patent and that said Letters Patent is hereby corrected as shown below:

Column 17, line 53; change "IR(CHCl$_3$)3733," to ---IR(CHCl$_3$):3733---.

Column 17, line 61; change "(s,3H,-CO$_2$Me), 3.68" to ---(s,3H,-CO$_2$$\underline{Me}$), 3.68---.

Column 17, line 62; change "-CO$_2$Me), 3.20" to --- -CO$_2$$\underline{Me}$), 3.20---.

Column 17, line 63; change "Hz,-CH$_2$-CH$_2$-), 2.75" to ---Hz,-C$\underline{H}_2$-CH$_2$-), 2.75---.

Column 17, line 64; change "$_2$-CH-)), 2.71 (t,2H, J=6.70 Hz, -CH$_2$-CH$_2$-)." to --- $_2$-C$\underline{H}_2$-), 2.71 (t,2H, J=6.70 Hz, -C$\underline{H}_2$-CH$_2$-).---.

Column 17, line 65; change "CDCl$_3$) 193.5" to ---CDCl$_3$):193.5---.

Column 17, line 66; change "142 4 (Cq)," to ---142.4 (Cq),---.

Column 17, lines 67-68; insert ---127(CH),--- between "127.2 (CH)" and "125.9 (Cq)".

Column 18, line 10; change "CDCl$_3$)$\delta$8.57" to ---CDCl$_3$):$\delta$8.57---.

Column 18, line 15; change "6.46 dd," to ---6.46 (dd---.

Column 18, line 17; change "-CO$_2$Me), 3.22 (t, 2H, J=7.0 Hz, -CH-" to --- -CO$_2$$\underline{Me}$), 3.22 (t, 2H, J=7.0 Hz, -C$\underline{H}_2$-CH$_2$-), ---.

Column 18, line 18; change "-CH$_2$-CH$_2$-)." to --- -C$\underline{H}_2$-CH$_2$-).---.

UNITED STATES PATENT AND TRADEMARK OFFICE
CERTIFICATE OF CORRECTION

PATENT NO. : 5,021,586

DATED : June 4, 1991

INVENTOR(S) : James P. Albarella and Nan-Horng Lin

It is certified that error appears in the above-identified patent and that said Letters Patent is hereby corrected as shown below:

Column 18, line 19; change "$CDCl_3) \delta 190.4$ (CO)," to ---$CDCl_3): \delta 190.4(CO)$,---.

Column 19, line 3: insert ---(B)--- to the left of the formula.

In the abstract; paragraph 2, line 3 change "direction" to ---direct---.

Signed and Sealed this

Eighth Day of December, 1992

Attest:

DOUGLAS B. COMER

*Attesting Officer*     *Acting Commissioner of Patents and Trademarks*